United States Patent [19]
Benja-Athon

[11] Patent Number: 6,122,547
[45] Date of Patent: Sep. 19, 2000

[54] CONSOLIDATED ELECTRICAL-LEAD ACUPUNCTURE NEEDLE

[76] Inventor: Anuthep Benja-Athon, 210 E. 36th St., Ground Floor, New York, N.Y. 10016

[21] Appl. No.: 09/176,006

[22] Filed: Oct. 20, 1998

[51] Int. Cl.$^7$ ..................................................... A61B 17/34
[52] U.S. Cl. ................................................................. 607/46
[58] Field of Search ........................... 128/907; 606/189; 600/377, 372, 373; 607/46, 115, 116

[56] References Cited

U.S. PATENT DOCUMENTS

| | | | |
|---|---|---|---|
| 5,094,242 | 3/1992 | Gleason et al. | 600/377 |
| 5,211,175 | 5/1993 | Gleason et al. | 600/377 |

*Primary Examiner*—George Manuel

[57] ABSTRACT

A single unit, integrated electrical-lead acupuncture needle comprises a first electrical lead member as the first physical continuation of a second electricity-conducting shaft member of a needle trocar. The first electrical lead member adaptable to variably adjust and change the length of the second shaft member of the needle trocar. A rigid plastic cannular handle member comprises a bore and a first bevelled opening for the passage of the electricity-conducting shaft member and a second square opening for the passage of the electricity-conducting shaft member and the electrical lead. One portion of the shaft member is housed and fits in the bore and the other portion of the shaft member extends beyond the bevelled first opening of the cannular handle member. The length of the shaft member can be variably changed and adjusted by incrementally extending from and retracting into the bore so that entire length including the tapered sharp tip can be housed in and sheathed within the bore of the cannular handle member. The electrical lead comprises a first enlarged and fixed spiral stopper portion to encumber the electrical lead beyond the bore of the handle. The second shaft member comprises a second enlarged and fixed spiral stopper portion to encumber second electricity-conducting shaft member beyond the bore of the handle. The third stopper is the second square opening of the cannular handle member. The device includes adhesive on the handle for reversibly affixing the unit to the skin of human.

10 Claims, 2 Drawing Sheets

CONSOLIDATED ELECTRICAL-LEAD ACUPUNCTURE NEEDLE

FIELD OF INVENTION

A consolidated electrical-lead acupuncture needle to reduce or eliminate the transmission of diseases in acupuncture.

BACKGROUND OF THE INVENTION

U.S. Pat. No. 5,857,968 issued Jan. 12, 1999 entitled Coupling Device in Electroacupuncture and U.S. Pat. No. 5,961,453 entitled Tandem Irreversible Coupling Device in Electroacupuncture issued Oct. 5, 1999 to this applicant.

The first objective is to provide a coupling device in electroacupuncture to eliminate the transmission of infectious organisms such as bacteria, virus, fungus between patients and acupuncturists in electroacupuncture.

The second objective is to provide easy-to-use, single-use, disposable, recyclable consolidated electrical-lead acupuncture needle and, therefore, compel the disposable of all instruments after the application on a patient in acupuncture.

The third objective is to provide an easy-to-use, effective, reliable, fixed, i.e. immovable, consolidated electrical-lead acupuncture needle to ensure the ease and safety of application and to achieve the above objectives.

The fourth objective is to provide effective, optimal, and reliable electrical connection and contact between the electrical lead and the acupuncture needle and, therefore, ensuring the correct and optimal delivery of electrical current from the electrical lead to the acupuncture needle and pin in electroacupuncture.

"Acupuncture has been used by millions of American patients and performed by thousands of physicians, dentists, acupuncturists, and other practitioners for relief of prevention of pain and for a variety of health conditions." (National Institutes of Health Consensus Development Statement. Acupuncture. Nov. 3–5, 1997). The United States Food and Drug Administration has classified acupuncture pin as a medical device. The approval and consensus have resulted in tremendous growth of the application of acupuncture therapeutics by American acupuncturists.

LACK OF STERILE EQUIPMENT AND TECHNIQUE:

Transmission of infections and diseases in electroacupuncture between patients and acupuncturists is well documented in the scientific literature (Ernst E. et al. Life-threatening adverse reactions after acupuncture? A systematic review. Pain 71: 123–126, 1997). Two of the reasons are that there is a lack of sterile equipment and technique and the disregards for using sterile equipment and technique. The design deficiency of the prior art of acupuncture pin and equipment significantly contributed to aforementioned problems.

Presently, electroacupuncture using the micron-thick shaft of a metallic needle and pin being grasped by a relatively larger alligator clip of one end of an electrical lead are the most commonly tools used in America. Essentially, an acupuncture needle has a handle and a shaft with a bore and an acupuncture pin has a handle and a solid shaft. The electrical lead of prior art consisting of a plastic-insulated wire with one end connects to a grasping device such as an alligator clip and the opposite end connected to the electrical stimulator. To establish the flow of electrical current from the electrical lead to the shaft of the acupuncture needle, the alligator clip grasps onto the micron-thick shaft of the acupuncture needle for the purpose of transmitting electrical current from the stimulator via the wire, the grasping device, the acupuncture pin, into the patient.

First, the connection between alligator clip and the micron-thick shaft of the acupuncture needle and pin is loose and poor. The alligator clip is not designed for the purpose of grasping the micron-thin shaft of the acupuncture needle and pin whose diameter is too small to be effectively grasped by the alligator clip. As a result, unreliable delivery of correct ampere and voltage of the electrical current to the acupuncture needle and pin are common. Second, the contact parts of the alligator clip, after so many use, are often oxidized rendering the clip ineffective due to a barrier of a layer of nonconductive oxidized matters.

Breaching of the sterile technique is common. First, the alligator clip and the electrical lead, which are not sterile to start, will not fix to one position site of the shaft of the acupuncture needle and pin and will slide toward the acupuncture site of the skin during the application of the electrical lead leading to the contamination of the acupuncture skin site and, consequently, the transmission of infectious organisms via the acupuncture site of the skin. Second, the electrical lead and the alligator clip are reused from patient to patient. Eventhough the acupuncture needle and pin are sterile, the alligator clip and its electrical lead are not sterile.

The connection of acupuncture and alligator clip tend to swing loosely in the air without a means of attaching both instruments to the skin and, consequently, causing the weight of the electrical lead to easily dislodge the percutaneously implanted acupuncture needle and pin and exposing the sharp tip of the acupuncture needle and pin to inadvertently puncture the fingers of the acupuncturists resulting in the transmission of diseases in electroacupuncture.

The acupuncture needle and pin and, therefore, the sharp tip of the shaft are difficult to visualize especially in the clinical settings and, consequently, inadvertent puncture of the fingers of the acupuncturists is common leading to the transmission of diseases in electroacupuncture.

In brief, the design deficiency of the acupuncture needle and pin and the electrical lead of prior art promotes the transmission infection and diseases between patients and acupuncturists. The present invention solves the aforementioned problems.

SUMMARY OF THE INVENTION

The design deficiency of the prior art of acupuncture pin and equipment significantly contributed to transmission of infections and diseases in acupuncture between patients and acupuncturists.

A single unit, integrated electrical-lead acupuncture needle comprises 1) a first electrical lead member as the first physical continuation of a second electricity-conducting shaft member wherefore adaptable to variably adjust and change the length of said shaft member, 2) a rigid or semi-rigid plastic cannular handle member comprises a bore and a first bevelled opening at the first bevelled end for the passage of said shaft member and incrementally and successively the entire said shaft member, and a second square opening at the end of said bore for the passage of said shaft member and said electrical lead. One portion of said shaft member is housed and fits in the bore and the other portion of said shaft member is beyond said bevelled opening of the cannular handle member. The length of the [first] shaft member within said bore is dictated by the length of said handle member but the [second] shaft member beyond said bevelled opening can be variably changed and adjusted by incrementally extending from and retracting into said bore by pushing and pulling, respectively, [the] said electrical lead so that in the latter setting the entire length including the tapered sharp tip of said shaft member can be housed in and sheathed within said bore of said handle member. The electrical lead comprises a first enlarged and fixed spiral stopper portion to encumber the electrical lead beyond the bore of the handle. The second shaft member comprises a second enlarged and fixed spiral stopper portion to encumber second electricity-conducting shaft member beyond the bore of the handle. The third stopper is the second square opening of the handle member. The device includes adhesive on the handle for reversibly affixing the unit to the skin of human. Aforementioned features compel the acupuncturist to discard said unit after one single use on a patient.

PREFERRED EMBODIMENTS OF THE INVENTION

Figure 1:
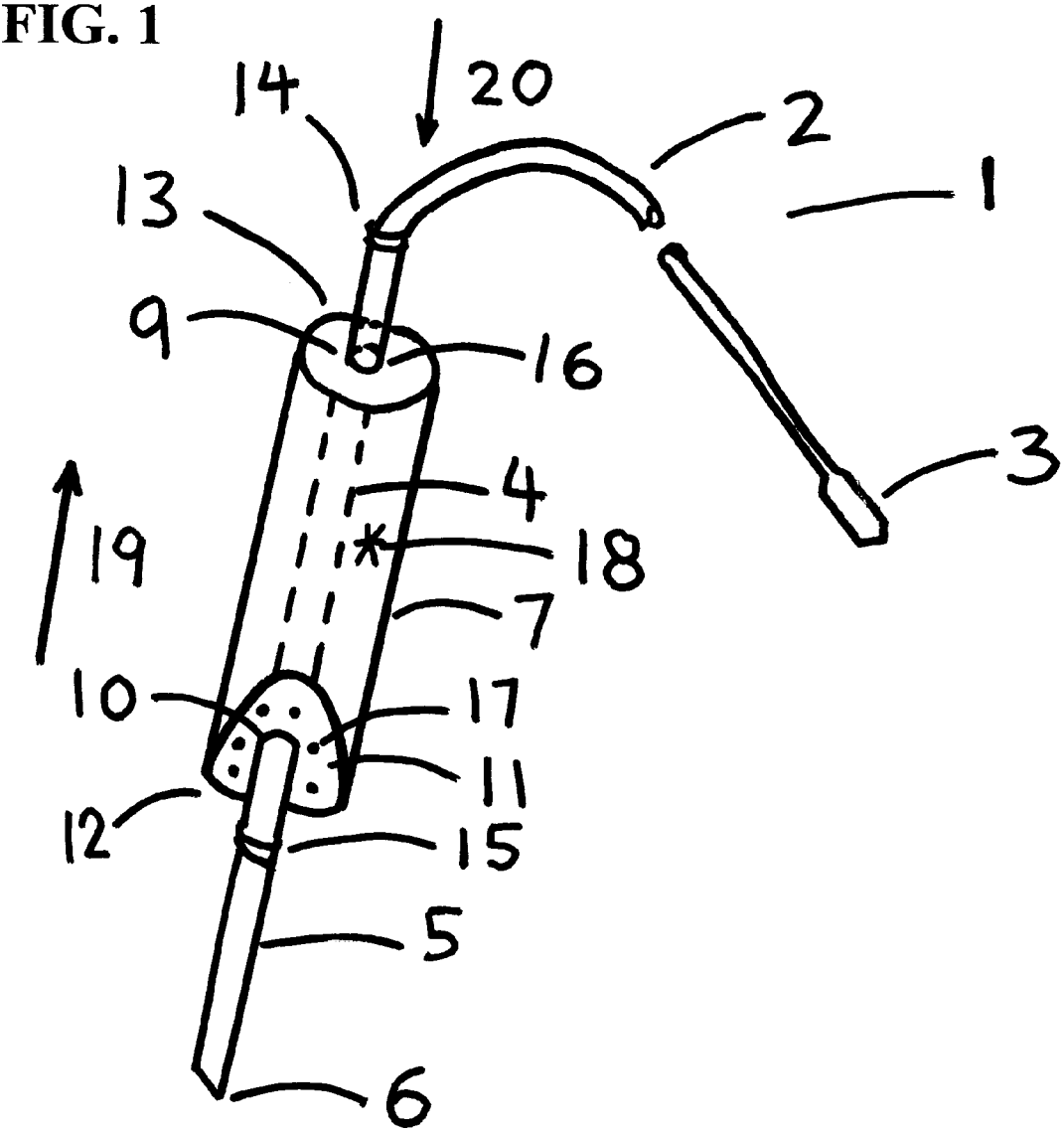
FIG. 1 is a perspective view of the present invention.

FIG. 1 shows the single unit, integrated electrical-lead acupuncture needle (device) 1 for performing acupuncture therapeutics in human or animal comprises a first electrical lead member 2 means of conducting electrical current via the connection means 3 from an electricity generating device (not shown) to the electricity-conducting shaft member device 1. Said first electrical lead member 2 is a physical continuation first shaft member 4 at the first end of the electricity-conducting first shaft member wherefore adaptable to variably adjust and change the length of the trocar-like second shaft member 5 which is a physical continuation of the second end of first shaft member 4. Shaft members 4 and 5 are needle or pin electrode manufactured from electricity-conducting metals and/or alloys. Shaft members 4 and 5 can be of two types—1) monopolar pin and monopolar needle, 2) concentric needle and concentric pin each of which comprises a cathode electrode and anode electrode. The range of cross-sectional diameters of shaft members 4 and 5 is about 0.05 mm–0.71 mm. The length of shaft member 4 is dictated by the length of handle member 7, however, the range of lengths of shaft member 5 is about 10–125 millimeters. The length of handle member 7 is about 0.5 inches although shorter or longer length can be provided. During the manufacturing process, the dimensions including cross-sectional dimension of electrical lead member 2 is adaptable to make said lead member 2 a physical continuation of the first end of the electricity-conducting first shaft member 4 without affecting the electricity conducting properties of lead member 2. Further to same, during the manufacturing process, electrical lead 2 is configured to function with either monopolar pin, monopolar needle, concentric needle electrode or concentric pin electrode.

Device 1 further comprises a rigid or semi-rigid plastic cannula-like handle member 7. Said handle member 7 comprises a bore 8 (see FIG. 2) and a first bevelled opening 10 at the first bevelled end 12 and a second square opening 9 at the second end 13 of handle member 7. First bevelled opening 10 is for the passage of the first shaft member 4 and incrementally and successively for the extension or retraction of the entire second shaft member 5 including the tapered sharp tip 6 into the bore of handle member 7. Second square opening 9 is for the passage of the first shaft member 4, electrical lead 2 and a proximal portion of second shaft member 5.

The second electricity-conducting shaft member 5 is a trocar-like physical continuation of said first electricity-conducting shaft member 4 extending beyond the first bevelled opening 10 of said handle member 7 and ending in a tapered sharp tip 6. The first shaft member 4 is housed and fits in the bore (see FIG. 2) of cannula-like handle member 7. The shaft member 5 by said virtues adaptable to percutaneously penetrate the skin and soft tissues during the acupuncture therapeutics and whose length can be variably changed and adjusted by incrementally retracting into as represents by single straight arrow 19 and extending from as represents by single straight arrow 20 the bore of handle member 7.

Electrical lead 2 comprises a first an enlarged and fixed spiral stopper 14 means of encumbering said electrical lead means beyond the bore of said handle means. Stopper 14 can be made from the same material as electrical lead 2 by the production similar, but not limited, to producing a metallic coiled spring. Stopper 14 prevents the excessive extension of the shaft member 5 by being obstructed by the square opening 9. Although square configuration is used, other configurations of the opening such as, but not limited to, circular can be used and has the diameter slightly smaller than the diameter of spiral stopper 14 so that stopper 14 cannot pass through a smaller cylinder of opening 9 as defined by said diameter or geometries.

The second stopper means of encumbering second electricity-conducting shaft member beyond the bore of said handle means is an enlarged and fixed spiral portion 15 of a length of said second electricity-conducting shaft member 5. As mentioned above, stopper 15 can also be made from the metallic shaft material by the production similar, but not limited, to producing a metallic coiled spring. The dimensions of the stopper 15 are slightly larger than the dimensions of circular or square opening 9 so that stopper 15 cannot pass through a smaller opening 9 as defined by said dimensions of opening 9. On the other hand, however, the diameter of bore 8 of handle member 7 is adaptable to allow stopper 15 to tightly slide proximally as represents by single arrow 19 within the bore of handle 7 to the opening 9 where stopper 15 is stopped. Therefore, entire second shaft member 5 including the tapered sharp tip 6 is covered by the bore of handle member 7 but cannot be disengaged from device 1 to exposed sharpened tip 6 which can advertently puncture the skin of the patient and acupuncturist. Further to same, said diameter of bore 8 of handle member 7 is adaptable to allow stopper 15 to tightly slide distally within the bore of handle 7 as represents by single arrow 20, The third stopper 16 means of encumbering said shaft members and electrical lead beyond said bore of said handle means is said second square or circular opening 9 of said cannula-like handle member 7 as defined supra.

Said stoppers 14 and 15 can also be made of other geometrical configurations such as, but not limited to, spherical or pear-shaped, and also from independent plastic or metallic materials which can be incorporated onto said members of device 1 to achieve the aforementioned purpose of said stoppers without departing from the spirit of the invention or the scope of the claims.

The dimensions of device 1 including those of electrical lead member 2, first shaft member 4, second shaft member 5, cannula-like handle member 7, stoppers 14 and 15 are so designed so that electrical lead 2, shaft members 4 and 5 and stoppers 14 and 15 can tightly but optimally fit, move, slide and operate within and outside the bore of member 7 to achieve the aforementioned goals and within spirit of the invention and the scope of the present invention and claims.

FIG. 1 further shows adhesive 17 on the bevelled surface 11 of handle member 7 for reversibly attaching and securing to the skin of a patient or the skin and integument of an animal during the acupuncture therapeutics. Adhesive 17 can be, but not limited to, the type of skin adhesive commonly used with colostomy bag and electrical pad in transcutaneous electrical stimulation. Bevelled surface 11 increases the surface area for the handle means 7 to have optimal contact with said skin and integument. Adhesive 17 can also be applied and incorporated to other parts of handle means 7 without departing from the spirit of the invention or the scope of the aforementioned claims. Adhesive 17 anchors device 1 to the skin and integument so that there is minimal movement of device 1 during acupuncture and also to eliminate the weight load on the device by the, albeit very light, weight of electrical lead 2 so that inadvertent dislodgement of the percutaneously implanted shaft member 5 is avoided and exposure of the sharp tip 6 to inadvertently puncture the fingers of the acupuncturists resulting in the transmission of diseases in electroacupuncture is eliminated.

Although it is not the feature claimed in the present invention, as it is a feature claimed in U.S. Pat. No. 5,857,968 issued Jan. 12, 1999 entitled the coupling device in electroacupuncture issued to this applicant, the consolidated electrical-lead acupuncture needle 1 can incorporate into said cannular handle the visualization enhancement materials and particles 18 such as, but not limited to, fluorescence, light-emitting substance, light-sensitive substance, light-activated substance and light-reflective substance.

Figure 2:
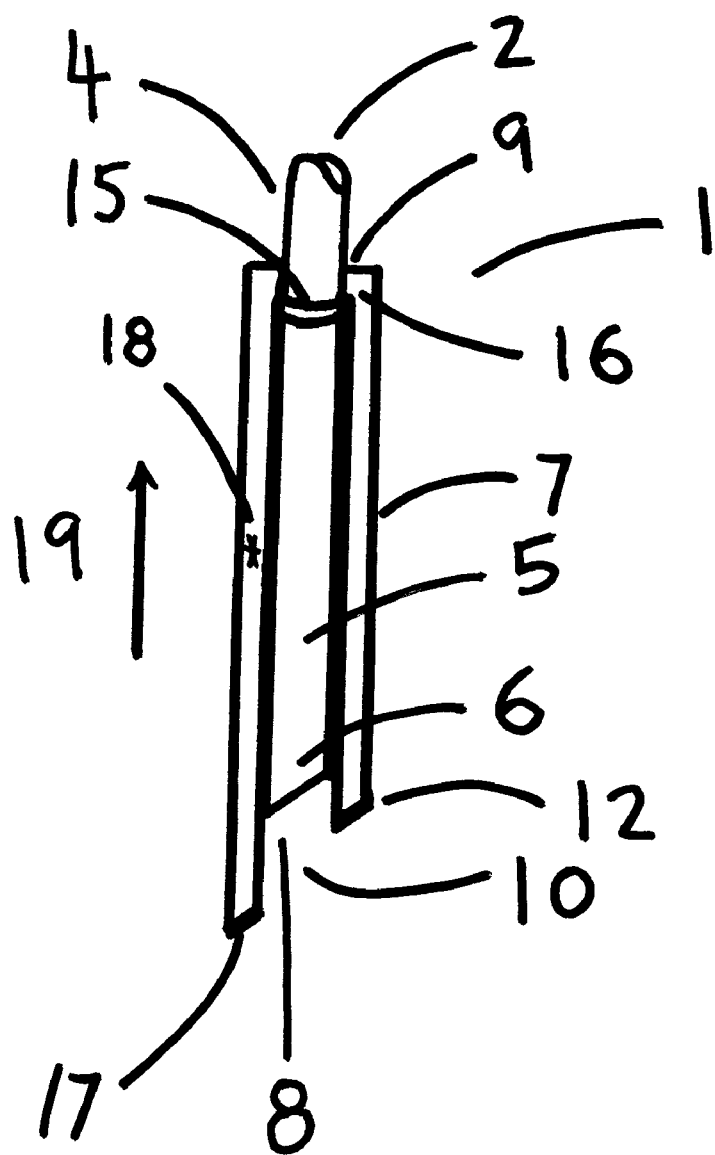
FIG. 2 is a midsagittal schematic view of the present invention.

FIG. 2 is a schematic view of device 1 as it is viewed from a plane perpendicular to the section of a plane perpendicular to the FIG. 1. FIG. 2 shows, by said virtues, the entire length including the tip 6 of shaft member 5 can be fully retracted as represents by a single arrow 19 and housed in and sheathed by the bore 8 of handle member 7. The diameter of the stopper 15 of shaft member 5 is slightly larger than diameter of square opening 9 so that stopper 15 cannot pass through a smaller cylinder as defined by said diameter of square opening 9 although the diameter of stopper 15 is less and adaptable to allow stopper 15 to slide proximally within bore 8 of handle 7 up to square opening 9 where stopper 15 is unyieldingly stopped square opening 9. Therefore, entire second shaft member 5 including the tapered sharp tip 6 is covered by the bore of handle member 7 but cannot be disengaged from device 1 to exposed sharpened tip 6 which can advertently puncture the skin of the patient and acupuncturist.

Device 1 is used as per standard sterile acupuncture technique using handle means 7 to percutaneously inserted shaft 5 into the tissues of a patient—human or animal. Said procedure and ease of insertion is facilitated and enhanced by the aforementioned features of device 1. In the complete circuit, an ammeter and a volt meter (not shown) are applied to register the change and flux in electrical current, and change in voltage and resistance as the acupuncture needle passes through various and different types of tissues possessing different electrical resistance in the body of a patient. The electrical current is from the electricity generating device (not shown) into lead 2 and shaft members 4 and 5 into said tissues. Aforementioned features of device 1 compels the acupuncturist to discard said unit after one single use on a patient.

After the electroacupuncture therapeutics, the acupuncture needle 1 is withdrawn from the skin and removed from the body of the patient and discarded as one single unit. Therefore, no reuse of the electrical lead and the acupuncture needle is allowed.

Although various preferred embodiments of this invention have been described, it will be appreciated by those skilled in the art that variations and adaptations may be made without departing from the spirit of the invention or the scope of the aforementioned claims.

Although the preferred techniques, stimuli, and instruments have been described in this application, it will be appreciated by those skilled in the art variations and adaptations may be made to said modes without departing from the spirit of the invention or the scope of the aforementioned claims.

What is claimed is:

1. A consolidated electrical-lead-acupuncture-needle means for performing acupuncture therapeutics in human or animal wherein a first electrical lead member means for conducting electrical current to said human or animal is a physical continuation of an electricity-conducting shaft member of a needle trocar member means for penetrating the skin of said human or animal, and wherein a first electrical lead member means for variably adjusting and changing the length of said shaft member beyond a first opening of a cannular handle member of said needle trocar member means incrementally extends and retracts said shaft member into a bore of said cannular handle member comprising:

said first electrical lead member means for conducting electricity which is a physical continuation of said electricity-conducting shaft member;

said cannular handle means;

said electricity-conducting shaft member of said needle trocar member which is a physical continuation of said first electrical lead member means;

a first stopper means for encumbering said electrical lead means beyond said bore of said cannular handle means;

a second stopper means for encumbering second electricity-conducting shaft member beyond a second opening of said cannular handle means;

a third stopper means for encumbering said shaft member and electrical lead beyond said bore of said cannular handle means; and adhesive means for reversibly affixing said consolidated electrical-lead-acupuncture-needle means to the skin and integument of said person or animal.

2. The consolidated electrical-lead-acupuncture-needle means for performing acupuncture therapeutics according to claim 1 comprises said first electrical lead member means for conducting electricity, said needle trocar comprising said electricity-conducting shaft member and said cannular handle member.

3. The consolidated electrical-lead-acupuncture-needle means according to claim 1 wherein said first electrical lead member means for conducting electrical current adaptable is an electrical lead adaptable to connect to an electricity generating device.

4. The consolidated electrical-lead-acupuncture-needle means according to claim 1 wherein said electricity-conducting shaft member of said needle trocar member comprises a first shaft member which is a physical continuation of said first electrical lead member means and is covered by said cannular handle member and, beyond said cannular handle member, a second shaft member having a free sharp end means for penetrating the skin of said human or animal.

5. The consolidated electrical-lead-acupuncture-needle means according to claim 1 wherein said cannular handle member of said needle trocar member is a rigid plastic tube comprises a first bevelled opening, a second opposite opening and a bore connecting said first and second openings, and wherein said bore houses and allows the movement of said first shaft member and said second shaft member in the directions toward and away from said first and second openings.

6. The consolidated electrical-lead-acupuncture-needle means according to claim 1 wherein said first stopper means for encumbering said electrical lead means beyond the bore of said cannular handle means is an enlarged and fixed spiral portion of a length of said electrical lead.

7. The consolidated electrical-lead-acupuncture-needle means according to claim 1 wherein said second stopper means for encumbering second electricity-conducting shaft member beyond said second opening of said cannular handle means is an enlarged and fixed spiral portion of a length of said second shaft member.

8. The consolidated electrical-lead-acupuncture-needle means according to claim 1 wherein said a third stopper means for encumbering said shaft member and electrical lead beyond said bore of said cannular handle means is said second opening of said cannular handle member.

9. The consolidated electrical-lead acupuncture needle according to claim 1 wherein said adhesive means for reversibly affixing said consolidated electrical-lead-acupuncture-needle means to the skin and integument of said person or animal is a skin and integument adhesive on said bevelled opening of said cannular handle member.

10. A consolidated electrical-lead-acupuncture-needle means for performing acupuncture therapeutics in human or animal wherein a first electrical lead member means for conducting electrical current from an electricity generating device to an electricity-conducting shaft member of a second needle trocar member is an integral component of said consolidated electrical-lead-acupuncture-needle means and wherein a first electrical lead member means for variably adjusting and changing the length of said shaft member beyond a first opening of a cannular handle member of said needle trocar member incrementally extends and retracts said shaft member into a bore of said cannular handle member comprising:

said first electrical lead member means for conducting electricity;

said cannular handle means;

said electricity-conducting shaft member of said needle trocar member;

a first stopper means for encumbering said electrical lead means beyond said bore of said cannular handle means;

a second stopper means for encumbering second electricity-conducting shaft member beyond a second opening of said cannular handle means;

a third stopper means for encumbering said shaft member and electrical lead beyond said bore of said cannular handle means; and adhesive means for reversibly affixing said consolidated electrical-lead-acupuncture-needle means to the skin and integument of said person or animal.

* * * * *